United States Patent [19]

Rosenthal

[11] Patent Number: 5,134,302
[45] Date of Patent: Jul. 28, 1992

[54] METHOD AND MEANS FOR GENERATING SYNTHETIC SPECTRA ALLOWING QUANTITATIVE MEASUREMENT IN NEAR INFRARED MEASURING INSTRUMENTS

[75] Inventor: Robert D. Rosenthal, Gaithersburg, Md.

[73] Assignee: Futrex, Inc., Gaithersburg, Md.

[21] Appl. No.: 588,628

[22] Filed: Sep. 26, 1990

[51] Int. Cl.⁵ ............................................. G01J 3/427
[52] U.S. Cl. ............................ 250/504 R; 250/495.1; 250/338.1
[58] Field of Search ............. 250/504 R, 495.1, 494.1, 250/338.1

[56] References Cited

U.S. PATENT DOCUMENTS

| | | | |
|---|---|---|---|
| 2,983,823 | 5/1961 | Oberly | 250/495.1 |
| 4,286,327 | 8/1981 | Rosenthal et al. | 250/338.4 |
| 4,620,104 | 10/1986 | Nordal et al. | 250/504 R |
| 4,627,008 | 12/1986 | Rosenthal | 250/338.1 |
| 4,627,284 | 12/1986 | Gersh et al. | 250/504 R |
| 4,742,235 | 5/1988 | Koji | 250/504 R |
| 4,922,116 | 5/1990 | Grinberg et al. | 250/504 R |

Primary Examiner—Jack I. Berman
Assistant Examiner—Kiet T. Nguyen
Attorney, Agent, or Firm—Rothwell, Figg, Ernst & Kurz

[57] ABSTRACT

A method and means for generating synthetic spectra allowing quantitative measurement utilizes dual chip alternatively energized IREDs with optical bandpass filter(s) passing two optical bands which could be combined with curvilinear interpolation to be utilized in a low cost small size quantitative measuring instrument.

7 Claims, 8 Drawing Sheets

METHOD AND MEANS FOR GENERATING SYNTHETIC SPECTRA ALLOWING QUANTITATIVE MEASUREMENT IN NEAR INFRARED MEASURING INSTRUMENTS

BACKGROUND OF THE INVENTION

1. Field of the Invention

This invention relates to improvements in near-infrared quantitative measuring instruments and particularly, to a method and means for generating synthetic spectra for such instruments.

2. Background and Prior Art

Near-infrared quantitative measuring instruments have been available for approximately 20 years. These instruments have proven to be highly accurate and simple to use for the measurement of chemical constituents in many different types of materials. For example, near-infrared instruments are commonly used in the grain industry for determining the protein of wheat and barley, in the food industry for measuring various organic constituents within food, in the chemical process industry to determine the chemical constituents within a production product, and in the medical field for non-invasively determining such items as body fat percentage.

There are three general types of near-infrared measuring instruments. Reflectance-type instruments normally measure between 1,100 and 2,500 nanometers to provide accurate measurement of materials that have a consistent surface and require access to only one side of the product being measured. Transmission-type measurements are available that operate between 600 and 1,100 nanometers and are able to measure almost any type of product without sample preparation provided that access is available to both sides of the measured product. The third type of near-infrared instrument is the interactance type which normally operates between 600 and 1,100 nanometers. In this type of instrument, light energy is directed into a body of a product and on the same side of the body at some distance away, the internal reflected light is measured.

In any of the above-described type of near-infrared measuring instruments, the use of discrete filters or the use of full scanning instruments are known. An example of the use of a filter-type approach is shown in U.S. Pat. No. 4,286,327.

In many applications, either discrete filter or full scanning instruments will provide similar accuracy. However, there are some applications where the typical discrete filter-type instruments do not provide sufficient information. Examples of this are applications where advanced mathematical treatments such as Partial Least Square or Principle Component Analysis are applied. In such approaches, a large number of wavelengths are needed to provide the necessary calibration coefficients.

One major disadvantage of the full scanning instruments is that they are considerably more expensive than the discrete filter instruments. Thus, the desire has been to develop techniques that allow discrete filter instruments to provide the same sensitivity and versatility as full scanning instruments. One such approach is described in U.S. Pat. No. 4,627,008 where the use of curvilinear interpolation allows development of synthetic spectra from a discrete filter instrument.

However, in the measurement of very subtle constituents, e.g., non-invasive measurement of the level of glucose in the blood stream with a low cost portable instrument, accurate knowledge of spectra is required at many wavelengths. There is a need in the art to generate such spectra to provide a meaningful quantitative measuring instrument.

U.S. Pat. No. 4,286,327 teaches that a group of IREDs, each with a separate narrow bandpass filter in front of it, can be consecutively illuminated, thereby generating meaningful optical information. In such patent, a separate narrow bandpass filter is required for each wavelength to be measured. However, for a low cost portable instrument where broad spectrum information is required, it becomes essentially impractical to provide the number of narrow bandpass filters that are required. A size limitation, combined with the need for low cost, precludes such approach.

For example, research has shown that on some individuals, accurate measurement of blood glucose can be obtained by using a combination of wavelengths between 640 nanometers and 1,000 nanometers. These studies have also shown that different combinations of wavelengths are required for different individuals because of the body composition differences between people. For example, if cholesterol or glucose is desired to be measured, those constituents are in such minute quantities compared to the presence of water, fat and protein in the body that they are difficult to measure without multiple wavelengths. Thus, the need in the art exists to provide a low cost, portable, simple instrument and yet have the instrument provide the equivalent of wavelengths at every 1 nanometer between 640 to 1,000 nanometers so as to be useful over a broad population.

SUMMARY OF THE INVENTION

This invention provides a method and means for producing synthetic spectra for use in quantitative near-infrared measuring instruments which can be utilized in curvilinear interpolation instruments and which provide two wavelengths from a single IRED by using a dual chip IRED, and provide multiple outputs by utilizing dual bandpass filters with a single IRED. Thus, two wavelengths at a very narrow tolerance can be produced from a single IRED.

BRIEF DESCRIPTION OF THE INVENTION

FIG. 1(A) shows a spectra of blood glucose values for a first individual.

FIGS. 1(B) and 1(C) show an expanded view of the FIG. 1(A) spectra.

FIG. 2(A) shows a spectra of blood glucose values for a second individual.

FIGS. 2(B) and 2(C) show an expanded view of the FIG. 2(A) spectra.

FIG. 3(A) shows a spectra of blood glucose values for a third individual.

FIGS. 3(B) and 3(C) show an expanded view of the FIG. 3(A) spectra.

FIG. 4(A) shows a spectra of blood glucose values for a fourth individual.

FIGS. 4(B) and 4(C) show an expanded view of the FIG. 4(A) spectra.

FIGS. 5(A) and 5(B) are schematics of a dual chip IRED showing different arrangements of such IREDs with optical bandpass filters.

FIGS. 6(A) and 6(B) are typical spectra for both light emitting diodes (LEDs) and infrared emitting diodes (IREDs).

FIG. 7(A) is spectra of a typical narrow bandpass filter and 7(B) illustrates a special narrow bandpass filter for two different bands.

DETAILED DESCRIPTION OF THE PREFERRED EMBODIMENT

To study how many wavelengths are required for accurate quantitative measurement using IRED techniques, an interactive study of accuracy of generating a synthetic spectra using the curvilinear approach taught by U.S. Pat. No. 4,637,008 versus actual spectra in different people was performed. For example, in wavelengths between 640 to 1,000 nanometers, it was found that 12 discrete wavelengths properly located in the spectra can generate a synthetic spectra that is equal in accuracy to when one "real spectra" is compared to another "real spectra." ("Real spectra" is defined as a spectra obtained from a high quality scanning spectrophotometer.)

For typical people, it was discovered that the following 12 wavelengths would provide the basis for generating synthetic spectra. (These wavelengths allow some reasonable tolerance, approximately ±2 nanometers each.) These wavelengths are set forth in the following table.

TABLE I

| GROUP A | | GROUP B | |
|---|---|---|---|
| Filter Number | Wavelength | Filter Number | Wavelength |
| 1 | 640 nm | 7 | 878 |
| 2 | 688 | 8 | 916 |
| 3 | 698 | 9 | 946 |
| 4 | 754 | 10 | 964 |
| 5 | 804 | 11 | 974 |
| 6 | 840 | 12 | 1000 |

FIGS. 1(A)-(C) through FIGS. 4(A)-(C) contain spectra from four different individuals, respectively, covering a broad range of race, body composition and gender. Each of the figures provide an overlay of "real data," i.e., data which was actually measured by a scanning spectrophotometer at every one nanometer interval, represented in an expanded scale, with a synthetic spectra generated using a curvilinear technique utilizing the 12 wavelengths set forth above. On each of these curves in FIGS. 1(A)-(C) through FIGS. 4(A)-(C), the correlation squared term (RxR) is given as well as the standard error between the "real data" versus the synthetic spectra. As can be seen, the synthetic spectra is very accurate as compared to the real spectra.

Also presented in FIGS. 1(A)-(C) through 4(A)-(C) are the R squared and the standard error of one real spectra overlayed with another real spectra of the same individual, represented as "Real vs. Real", at approximately the same period in time (measured within a few minutes of each other). (Note the figures do not show the curves of the real spectra overlaying.) As illustrated in FIGS. 1(A)-(C) through 4(A)-(C), the synthetic spectra and the real spectra accuracy numbers are quite close to the accuracy number between two real spectra. Moreover, when regression analysis against known blood glucose values was performed with the synthetic spectra analysis of the present invention, it provided essentially identical accuracy as such analysis using real spectra.

Figure 1A:
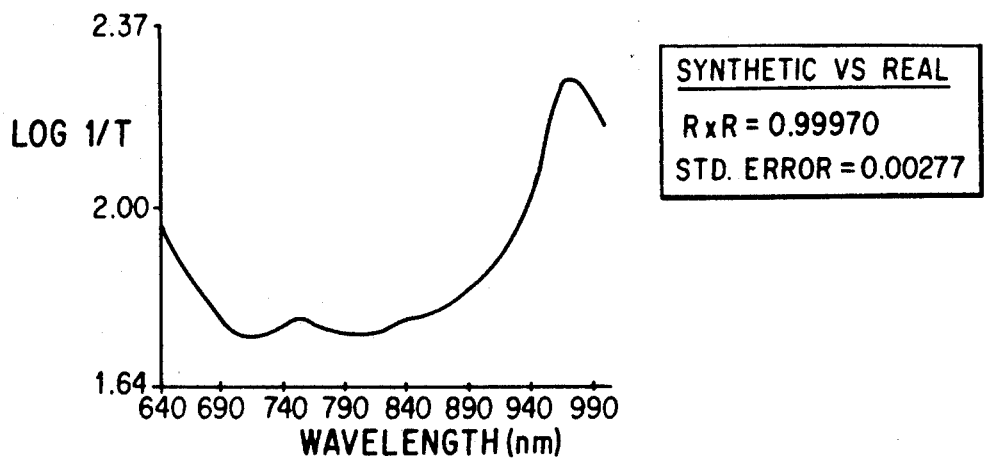
Figure 1B:
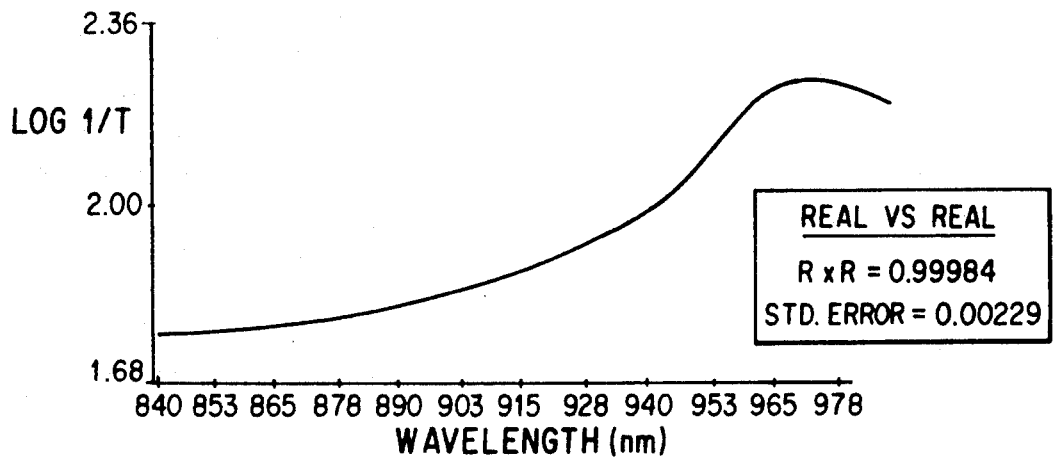
Figure 1C:
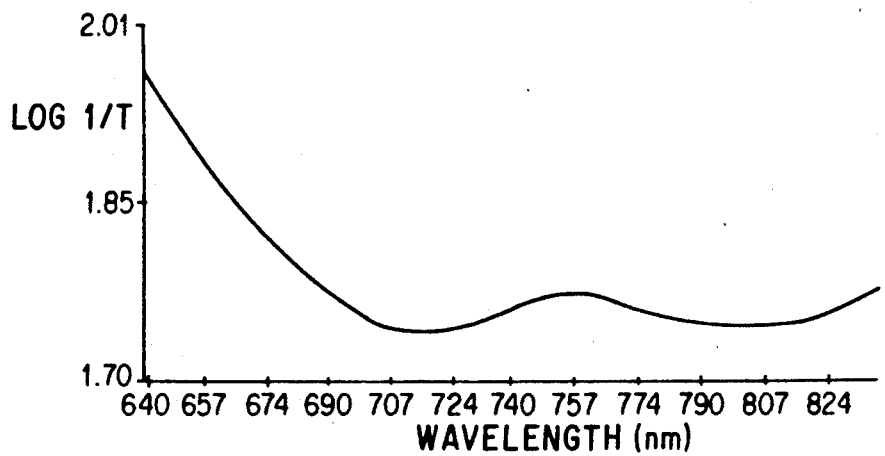
Figure 2A:
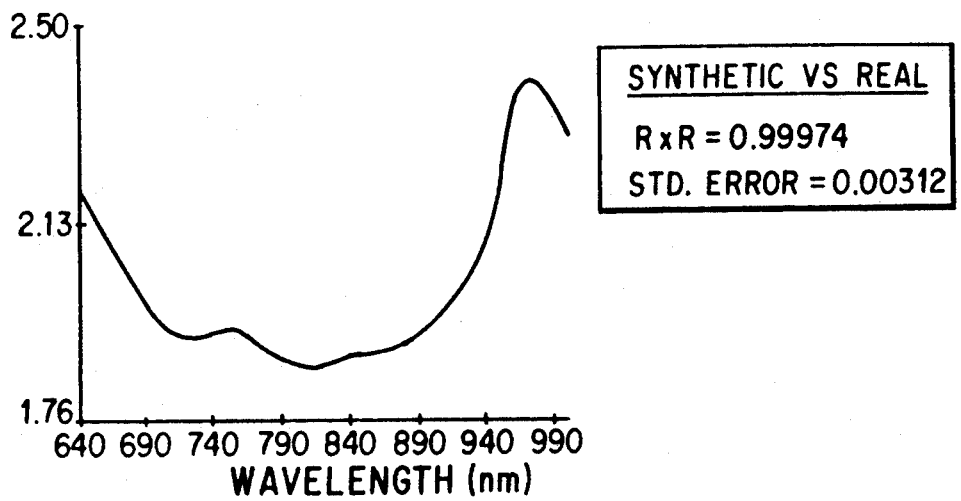
Figure 2B:
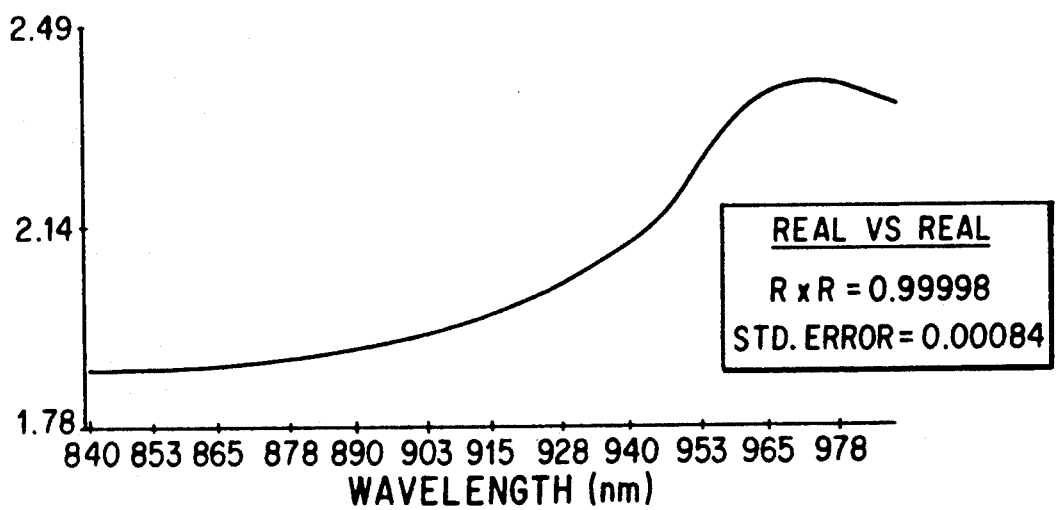
Figure 2C:
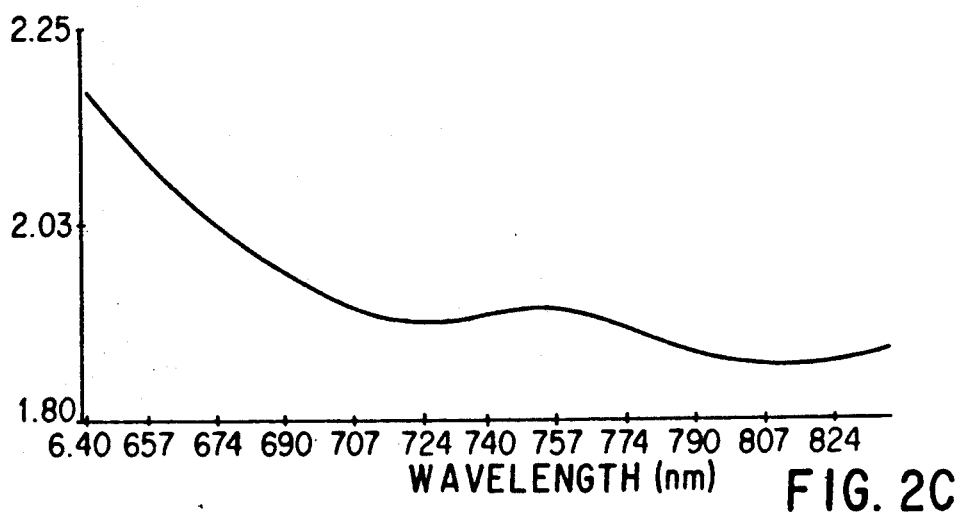
Figure 3A:
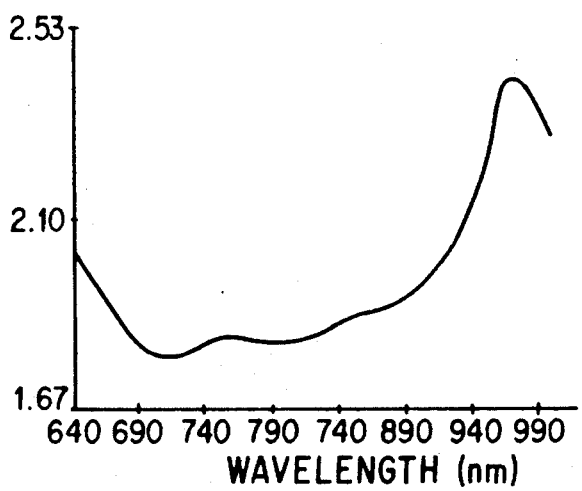
Figure 3B:
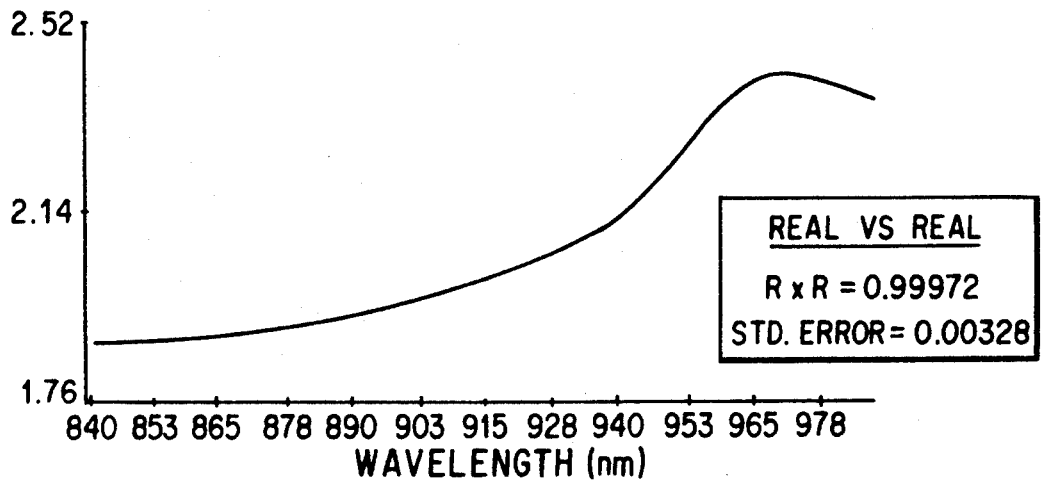
Figure 3C:
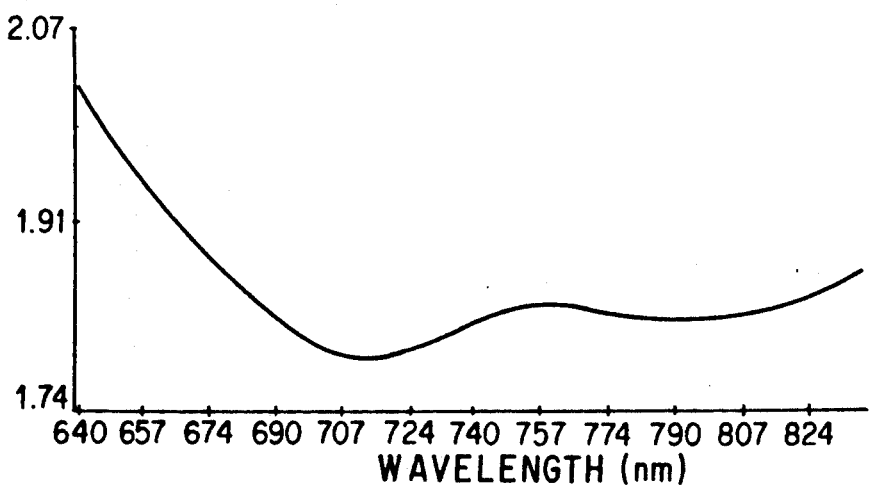
Figure 4A:
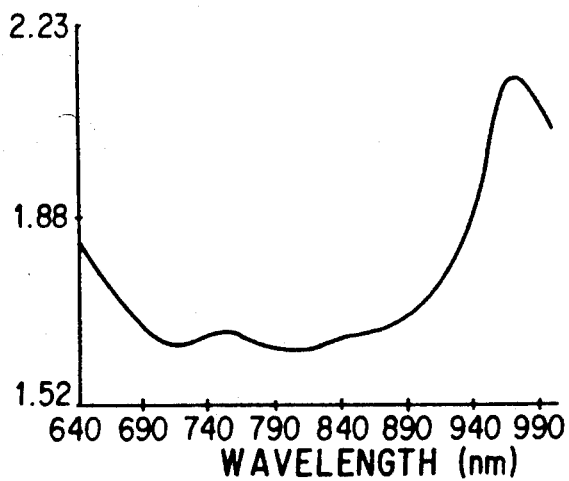
Figure 4B:
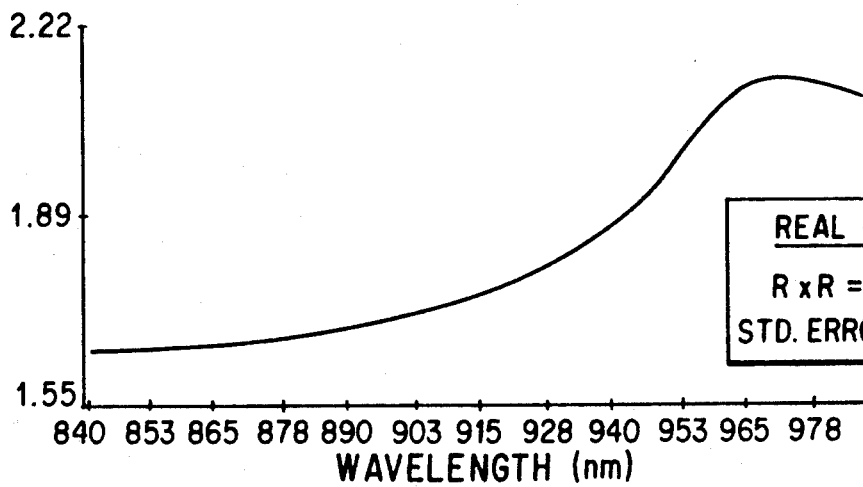
Figure 4C:
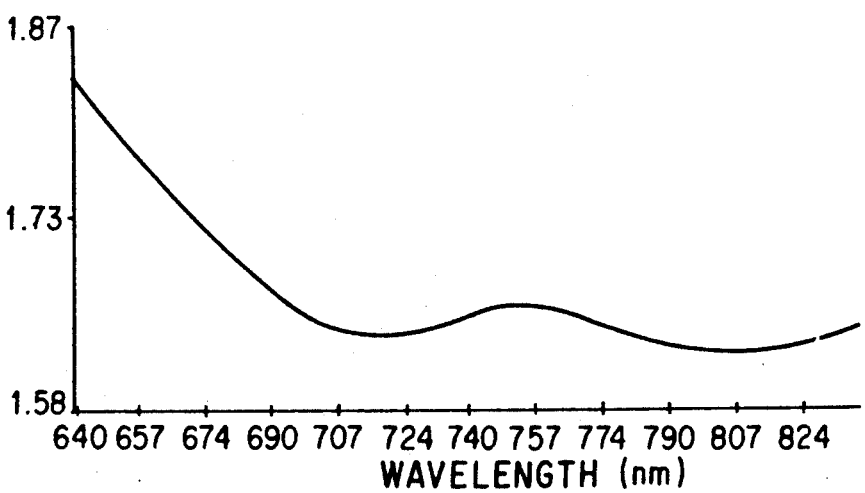
Figure 5A:
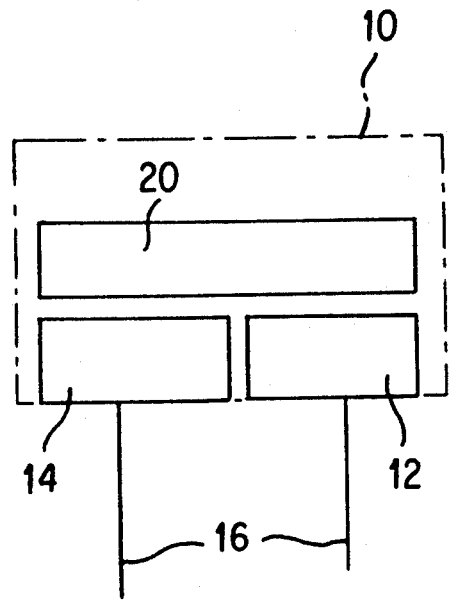
Figure 5B:
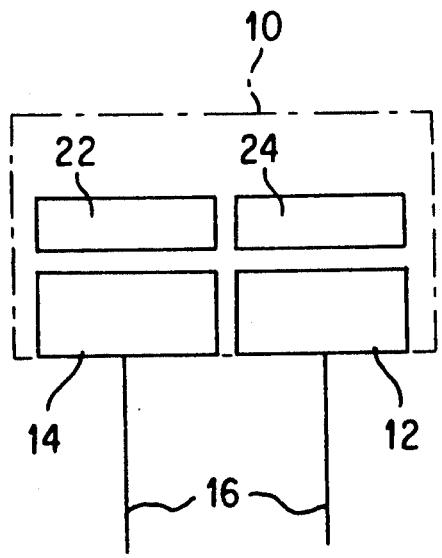

A low cost method of implementing this invention is shown in FIGS. 5(A) and 5(B). In each of these figures, there is shown a light emitting diode 10 using two light emitting chips 12 and 14 in the single diode. The chips may be alternately energized through leads 16 as is known in the art. For example, a single diode may be obtained on the market that provides both red and green light, depending on the way it is powered. In FIGS. 5(A) and 5(B), the single diode 10 comprises the two chips 12 and 14. Chip 14 would provide energy in the region of wavelengths Group A and chip 12 would provide energy in the region of wavelengths Group B from Table I above.

Figure 6A:
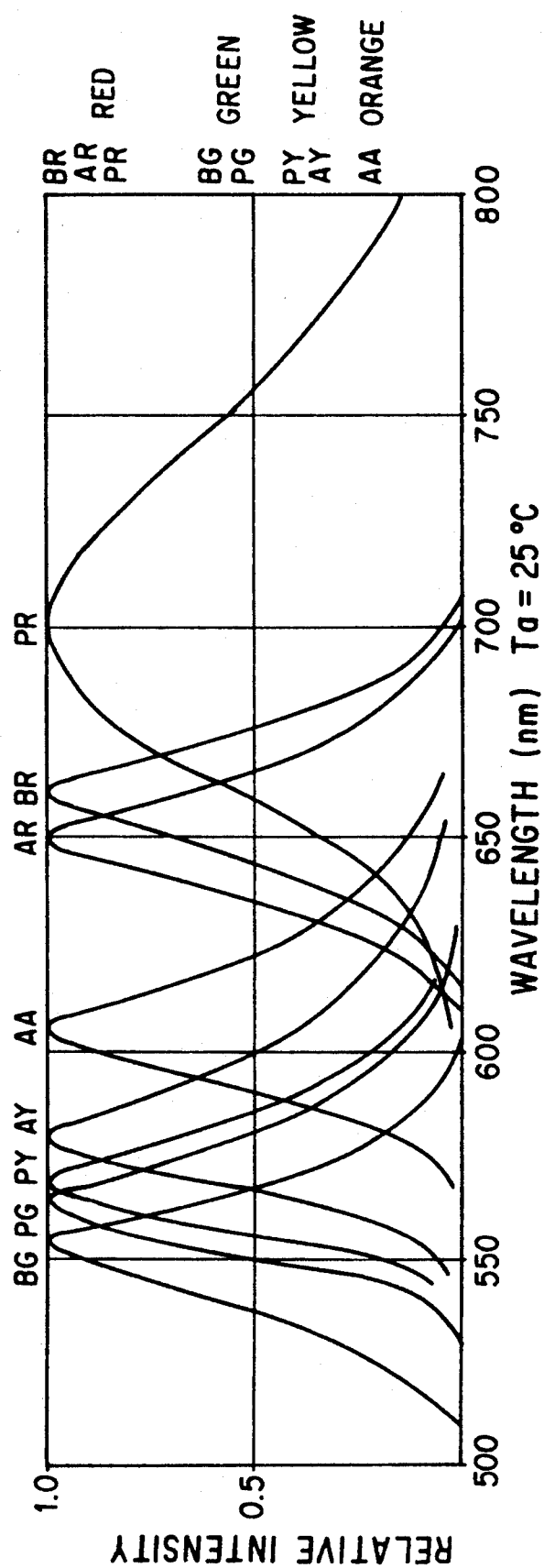
Figure 6B:
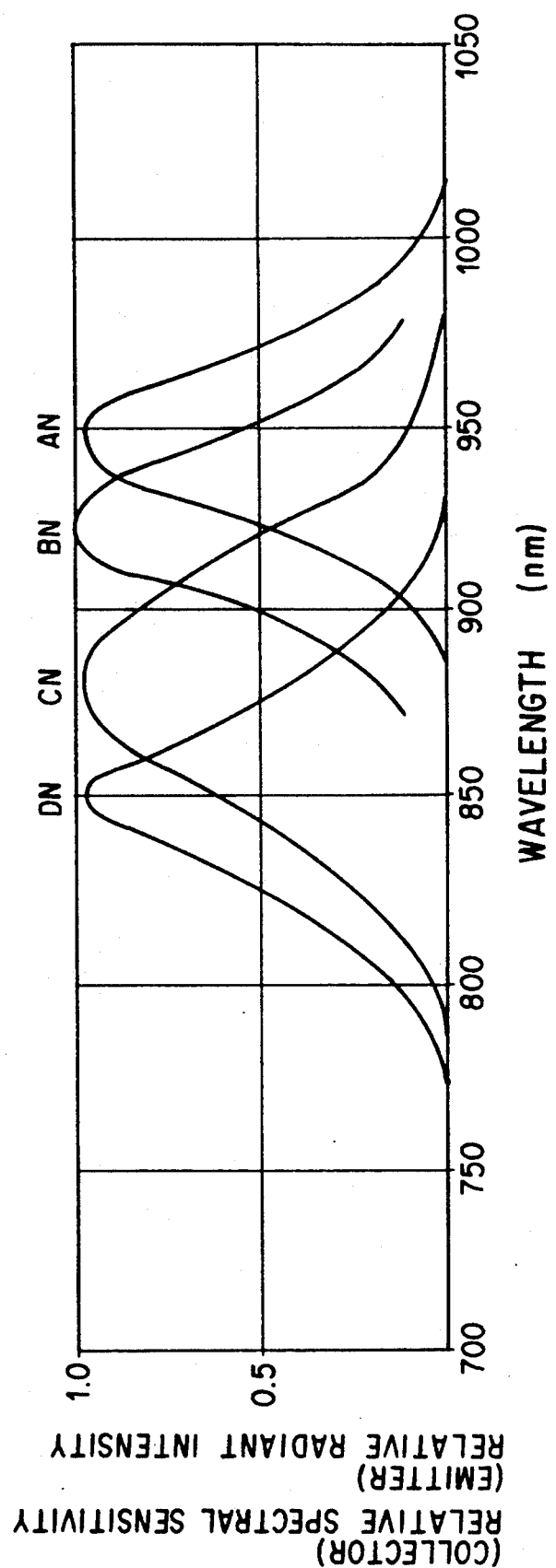

This can be further understood with reference to FIGS. 6(A) and 6(B) which are taken from "Opto Electronic Components Data Book 1988" of Stanley Electric Co., Ltd. In these figures, typical spectra for both LEDs and IREDs are shown. For example, wavelength #6 and wavelength #12 from Table I above can be generated using two chips 12 and 14 in a single IRED 10, namely chips AN and DN. Thus, the wavelength region for wavelength #6 in Table I would be from the chip DN, i.e., chip 14, and wavelength #12 would be a chip of the characteristics AN, i.e., chip 12.

Set forth below in Table II are the same wavelengths as in Table I above, but with the corresponding chips selected from FIGS. 6(A) and 6(B). Stated differently, depending on how the IRED is powered, i.e., whether chip 12 or chip 14 is energized, either energy for wavelength 12 or wavelength 6 is illuminated.

TABLE II

| GROUP A | | | GROUP B | | |
|---|---|---|---|---|---|
| Filter Number | Wavelength | | Filter Number | Wavelength | |
| 1 | 640 nm | AR or BR | 7 | 878 | CN or DN |
| 2 | 688 | BR or PR | 8 | 916 | CN or BN |
| 3 | 698 | PR | 9 | 946 | AN or BN |
| 4 | 754 | PR | 10 | 964 | AN or CN |
| 5 | 804 | PR or DN | 11 | 974 | AN |
| 6 | 840 | DN Type | 12 | 1000 | AN Type |

Figure 7A:
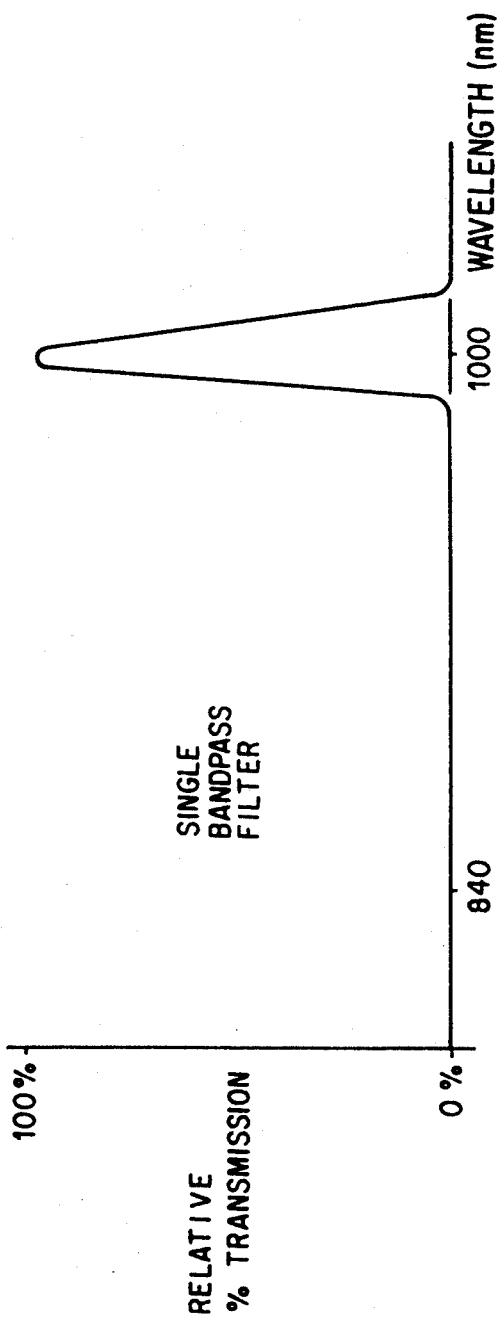
Figure 7B:
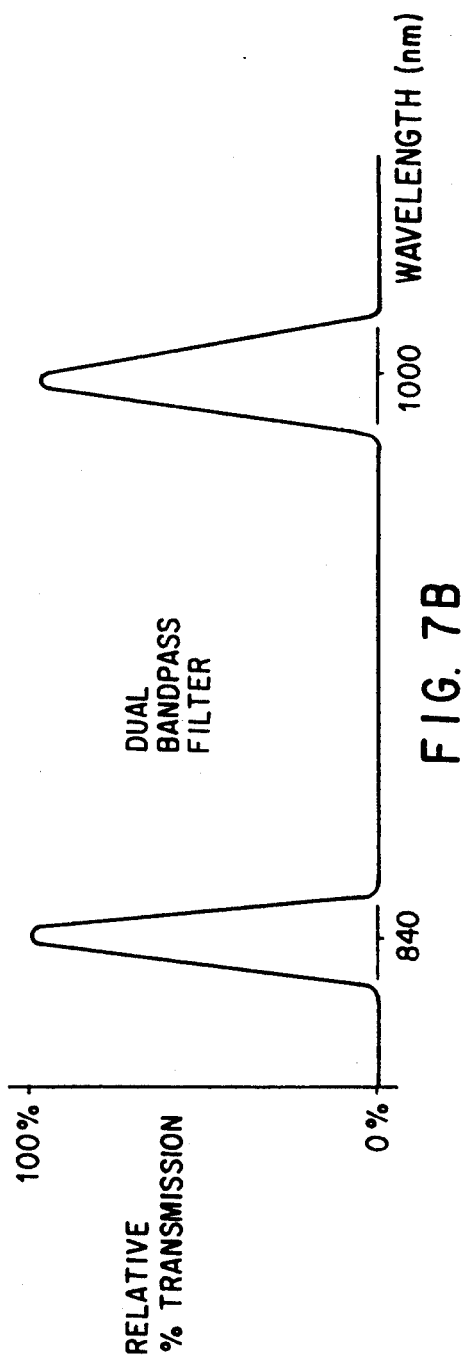

Also as shown in FIG. 5(A), there is a bandpass filter 20 with two bandpasses. While in FIG. 5(B), there are separate optical bandpass filters 22 and 24, filter 22, for example, with a bandpass for #6 wavelength in the table above, and optical filter 24 with a bandpass for #12 wavelength in the table above. The bandpass filter 20 of FIG. 5(A) could pass two bands, for example, as shown in FIG. 7(B). In other words, FIG. 7(A) illustrates a spectra of a typical narrow bandpass filter which would be filter 24 in FIG. 5(B) FIG. 7(B) illustrates the transmission from a special narrow dual bandpass filter that allows light to pass at two different bands, e.g., 840 and 1,000 nanometers.

When the dual chip IRED in FIG. 5(A) is utilized in a single filter with two bandpasses as shown in FIG. 7(B), and when the first chip of the IRED is illuminated, wavelength #6 is available. When that chip is de-energized and the second chip is powered, then wavelength #12 of the above table is illuminated.

Utilizing this invention, only 6 IREDs and 6 filters are required to generate the identical data that would normally take 12 optical filters in combination with 12 individual IREDs. Thus, the number of parts is reduced by a factor of 2 which means a significant increase in reliability as well as the cost being reduced by a factor of 2. Moreover, this invention reduces the space requirements and such is essential for a portable pocket-size instrument.

It is the intention not to be limited by this specific embodiment but only by the scope of the appended claims.

I claim:

1. A method of providing synthetic spectra for use in a curvilinear interpolation near-infrared quantitative measuring instrument, the method comprising, providing two wavelength IRED emissions from a single source, and filtering the output of such source into two separate wavelengths.

2. A means for providing synthetic spectra for use in curvilinear interpolation instrument that comprises a dual chip IRED in combination with a dual bandpass filter.

3. A quantitative near-infrared measuring instrument of the type utilizing IREDs with the improvement comprising a dual chip IRED providing two separate wavelengths.

4. A measuring instrument as defined in claim 3, further comprising an optical bandpass filter means filtering the output of the dual chip IRED.

5. A measuring instrument as defined in claim 4 utilizing two separate filters, each with a single bandpass in connection with a dual chip IRED providing two wavelengths.

6. A measuring instrument as defined in claim 4, further comprising a single optical bandpass filter with two bandpasses.

7. A measuring instrument as defined in claim 3, further utilizing curvilinear interpolation means.

* * * * *